ated Nemours and
United States Patent [19]

Apotheker

[11] 4,303,761
[45] Dec. 1, 1981

[54] FLUOROELASTOMER GELLING AGENTS AND PRODUCTS MADE THEREFROM

[75] Inventor: David Apotheker, Wilmington, Del.

[73] Assignee: E. I. Du Pont de Nemours and Company, Wilmington, Del.

[21] Appl. No.: 107,011

[22] Filed: Dec. 26, 1979

Related U.S. Application Data

[62] Division of Ser. No. 42,946, May 29, 1979.

[51] Int. Cl.³ ............................................. C08L 27/12
[52] U.S. Cl. ..................................... 525/200; 526/248
[58] Field of Search ......................... 525/200; 526/248

[56] References Cited

U.S. PATENT DOCUMENTS

| | | | |
|---|---|---|---|
| 3,814,722 | 6/1974 | Glaister et al. | 260/37 SB |
| 3,851,018 | 11/1974 | Kelly | 525/200 |
| 3,851,018 | 11/1974 | Kelly | 525/200 |
| 3,892,643 | 1/1975 | Tanaka et al. | 204/159.13 |
| 4,115,481 | 9/1978 | Finlay | 252/199 |
| 4,200,749 | 4/1980 | Flagg | 544/221 |

OTHER PUBLICATIONS

Derwent Abstract Su 520,362, published Nov. 10, 1976.
Derwent Abstract Su 504,771, published Jun. 29, 1976.
Derwent Abstract Su 381,668, published Aug. 14, 1973.

*Primary Examiner*—Harry Wong, Jr.

[57] ABSTRACT

Fluorinated allylisocyanurates are extremely efficient gelling agents for fluoroelastomers. Blends of fluorinated allylisocyanurate gelled fluoroelastomers with non-gelled fluoroelastomers have improved processability as compared with non-gelled fluoroelastomers and blends of other gelled fluoroelastomers with non-gelled fluoroelastomers.

6 Claims, 4 Drawing Figures

FLUOROELASTOMER GELLING AGENTS AND PRODUCTS MADE THEREFROM

This is a division of application Ser. No. 042,946, filed May 29, 1979.

DESCRIPTION

1. Technical Field

This invention relates to novel and extremely efficient gelling agents for fluoroelastomers, to gelled fluoroelastomers made with these novel gelling agents, and to blends of such gelled fluoroelastomers with non-gelled fluoroelastomers, which gelled fluoroelastomers and blends possess improved processing properties, particularly as compared with non-gelled fluoroelastomers, but even as compared with blends of non-gelled fluoroelastomers with fluoroelastomers gelled with agents other than the novel gelling agents of the present invention. In particular, the gelling agents of the present invention achieve extremely high levels, e.g., approximately 90%, of gel (i.e. crosslinking) with very low levels, less than 0.5 weight percent, of gelling agent. Fluoroelastomer blends made with these gelling agents exhibit improved extrusion and milling.

2. Background Art

U.S. Pat. No. 4,115,481, granted Sept. 19, 1978, to Finlay and Omura, discloses the use of bromotrifluoroethylene as a gelling agent for certain fluoroelastomers and peroxide curable fluoroelastomer blends of non-gelled fluoroelastomer with bromotrifluoroethylene gelled fluoroelastomer. Such blends are disclosed as offering improved milling and extrusion properties. The bromotrifluoroethylene gelled fluoroelastomer of Finlay and Omura, however, exhibits a gel content of only about 50-65% even though up to 3% by weight of gelling agent is used. In addition, although the blends disclosed by Finlay and Omura offer improved processability in rubber mills and extruders as compared with prior fluoroelastomer compositions, the blends of the present invention exhibit further improvements in processability.

U.S. Pat. No. 3,851,018, granted Nov. 26, 1974, to Kelly discloses the use of certain perfluorodivinyl ethers of the formula $$CF_2=CF-O(CF_2)_n-O-CF=CF_2$$

where n is an integer from 2-24 as gelling agents for certain fluoroelastomers and also discloses blends of non-gelled fluoroelastomers with perfluorodivinylether gelled fluoroelastomers. Such blends are disclosed as offering improved milling and extrusion properties. As with the gels of Finlay and Omura, the gelled fluoroelastomers exemplified by Kelly exhibit a gel content of only about 50% even though up to 20% by weight of gelling agent is used, and although the blends disclosed by Kelly offer improved processability as compared with prior fluoroelastomer compositions, the blends of the present invention exhibit further improvements in processability. Further, although Kelly does disclose that fluoroelastomers with a gel content of up to 100% would be useful, there are no examples of such fluoroelastomers; and even if Kelly's gelling agent could produce a 100% gelled fluoroelastomer, it would only be possible with excessive quantities of gelling agent.

DISCLOSURE OF THE INVENTION

The present invention relates to novel and extremely efficient gelling agents for fluoroelastomers, the gelling agents being hexafluorotriallylisocyanurate, 1,3,5-tris-(3,3,-difluoro-2-propenyl)-s-triazine-2,4,6-(1H,3H,5H)-trione, hereinafter HFTAIC,

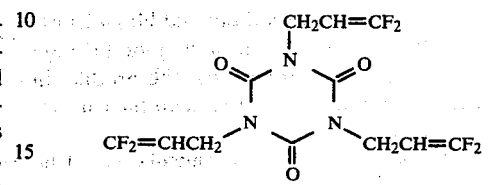

and N-methyltetrafluorodiallylisocyanurate, 1,3-bis-(3,3-difluoro-2-propenyl)-5-methyl-s-triazine-2,4,6-(1H,3H,5H)-trione, hereinafter TFDAIC,

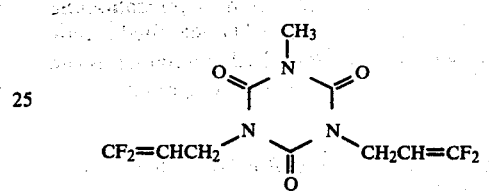

to HFTAIC and TFDAIC gelled fluoroelastomers, to curable blends of non-gelled fluoroelastomers with HFTAIC and TFDAIC gelled fluoroelastomers, to methods of making HFTAIC and TFDAIC, to the process of making gelled fluoroelastomers using HFTAIC or TFDAIC, to the process of making curable fluoroelastomer blends using HFTAIC or TFDAIC gelled fluoroelastomers and to vulcanized articles made from such blends. It should be understood that by HFTAIC or TFDAIC gelled fluoroelastomers there is meant partially gelled fluoroelastomers as well as those substantially completely gelled fluoroelastomers. As is discussed hereinafter, a gel content of at least 50% in the gelled fluoroelastomer is generally required to realize the significant improvements made possible by the present invention.

The preferred novel gelling agent of the present invention, HFTAIC, can be prepared in a four step synthesis which is summarized by the following schematic equations:

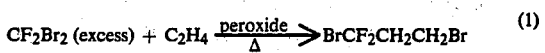

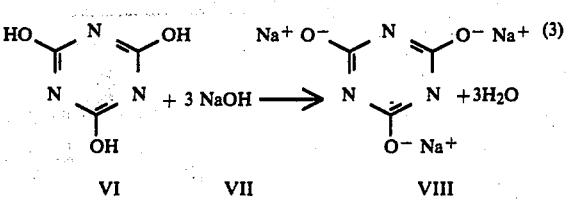

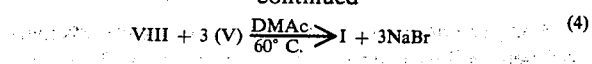 (4)

Details concerning the preparation of dibromodifluoropropane as shown schematically in equation (1) above can be found in an article by Blomquist and Longone, JACS, 97, 4981 (1957).

An alternative to the process described above starts with chlorobromodifluoromethane and goes through substantially the same steps except that the product in step (2) is chlorinated (not brominated) and the catalyst in step (4) is LiBr/DMAc.

A further alternative to steps (3) and (4) would be cyclization of an isocyanate:

V + KOCN $\xrightarrow{DMAc}$ I (4')

A more preferred two step synthesis of HFTAIC is disclosed in copending U.S. Patent Application Ser. No. 042,947 now U.S. Pat. No. 4,211,868, filed simultaneously herewith by John Paul Erdman, which is summarized by the following schematic equations:

 (1)

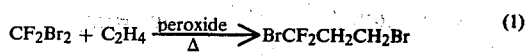 (5)

Alternatively, the cyanuric acid (compound VI) can be converted to the sodium salt which is, in turn, converted to the desired HFTAIC:

 (3)

IV + VIII $\xrightarrow[base]{DMAc}$ I (5')

It should be noted that in the reactions represented by equation (5') above, the base can be eliminated, but generally this will be accompanied by a considerable loss of yield.

The less preferred gelling agent of the present invention, TFDAIC, can be prepared in a three step synthesis which is summarized in the following schematic equations:

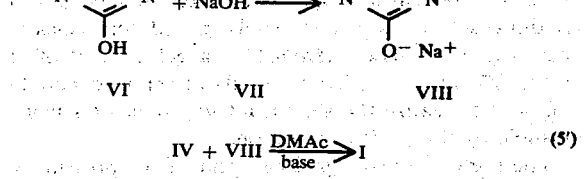 (6)

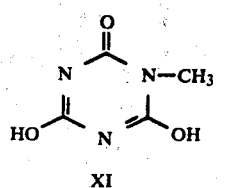

XI

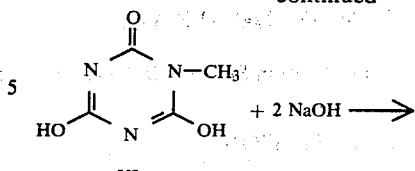 (7)

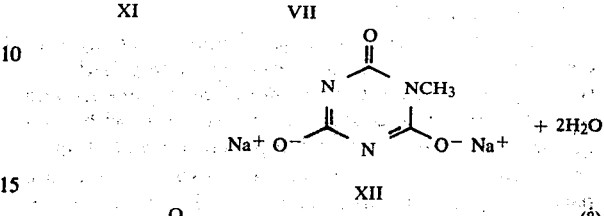

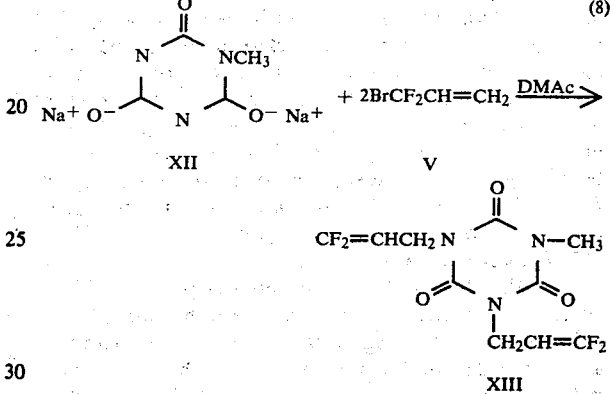 (8)

Details of the reaction shown in (6) can be found in W. J. Close, JACS, 75 3617 (1953).

As indicated above, HFTAIC is preferred over TFDAIC, because it provides three sites of unsaturation per molecule, rather than two, and is therefore a more efficient gelling agent. One would have to use a greater molar quantity of TFDAIC than would be required if one used HFTAIC to achieve otherwise equivalent results.

As stated above, HFTAIC and TFDAIC are extremely efficient gelling agents for fluoroelastomers. Fluoroelastomers which can be efficiently gelled with HFTAIC or TFDAIC include those copolymers with interpolymerized units consisting essentially of vinylidene fluoride units, at least one type of fluorine containing olefin unit, and, optionally, units selected from one or more of the following: perfluoroalkyl perfluorovinyl ethers, bromotrifluoroethylene and bromotetrafluorobutene. The novel gelling agent of the present invention can also be used to further gel partially gelled fluoroelastomers, such as those containing bromotrifluoroethylene or perfluorodivinyl ethers in addition to the interpolymerized units mentioned immediately above.

Preferred fluoroelastomers which can be efficiently gelled with HFTAIC or TFDAIC include copolymers with interpolymerized units derived from any of the following combinations:

(a) vinylidene fluoride and hexafluoropropylene or pentafluoropropylene;

(b) vinylidene fluoride, tetrafluoroethylene and hexafluoropropylene or pentafluoropropylene;

(c) vinylidene fluoride, perfluoroalkyl perfluorovinyl ethers, and at least one of hexafluoropropylene, pentafluoropropylene, and tetrafluoroethylene;

(d) vinylidene fluoride, perfluoroalkyl perfluorovinyl ethers, bromotetrafluorobutene, and at least one of hexafluoropropylene, pentafluoropropylene and tetrafluoroethylene; and (e) vinylidene fluoride, bromotetrafluorobutene, and at least one of tetrafluoroethylene and hexafluoropropylene.

For example, suitable polymers can be composed of about 30–70 weight % vinylidene fluoride units and about 70–30 weight % hexafluoropropylene units (see, e.g., U.S. Pat. No., 3,051,677, granted Aug. 28, 1962 to Rexford). Alternatively, suitable polymers can be composed of about 25–70 weight % vinylidene fluoride units, about 19–60 weight % hexafluoropropylene units, and about 3–35 weight % tetrafluoroethylene units (see, e.g., U.S. Pat. No. 2,968,649, granted Jan. 17, 1961 to Pailthorp and Schroeder). Alternatively suitable polymers can be composed of about 4–15 weight % tetrafluoroethylene units, about 48–65 weight % vinylidene fluoride units, about 8–23 weight % hexafluoropropylene units and about 17–30 weight % of perfluoroalkyl perfluorovinyl ether units wherein the alkyl group contains 1–5 carbon atoms (see, e.g., U.K. Pat. No. 1,496,084, complete specification published Dec. 21, 1977). Alternatively, suitable polymers can be composed of about 10–85 mole % vinylidene fluoride units, about 2–50 mole % of said perfluoroalkyl perfluorovinyl ether units, and about 3–80 mole % of a component consisting of one or more of the following: hexafluoropropylene units and tetrafluoroethylene units (see, e.g., U.S. Pat. No. 3,235,537, granted Feb. 15, 1966 to Albin and Gallagher). Alternatively, suitable polymers can be composed of up to 3 mole % of bromotrifluoroethylene units or bromotetrafluorobutene units incorporated into polymers as described immediately above (see, e.g., U.S. Pat. No. 4,035,565, granted July 12, 1977 to Apotheker and Krusic).

The HFTAIC and TFDAIC gelled fluoroelastomers of the present invention are prepared so that their gel content is greater than 50%, preferably so that the gel content is from 80–95%, and most preferably between 85–90%. The gel content is determined as follows: a solution-dispersion of a known concentration (about 1% by weight polymer) in methyl ethyl ketone is placed in a closed centrifuge tube and centrifuged at about 17,000 rpm (RCF 34,800×G) for one-half hour. The concentration of polymer in the supernatant liquid is determined by evaporation to dryness of a known volume. The amount of gel polymer is calculated from the difference in concentration of total polymer and concentration of polymer in the soluble portion.

A gel content of greater than 50% is generally achieved by incorporating into the fluoroelastomer 0.05–3.0% by weight of HFTAIC or TFDAIC. Where a fluoroelastomer with a gel content substantially above 90% is desired, one can use quantities of HFTAIC of TFDAIC at the higher end of the above-stated range. Fluoroelastomers with a significant gel content, i.e. at 50% of above, can generally be achieved with amounts of HFTAIC or TFDAIC as small as 0.05% by weight. Although one could use even less HFTAIC or TFDAIC, the processability of blends made therefrom is not likely to offer significant processability advantages as compared with non-crosslinked fluoroelastomer. As indicated above, for a given fluoroelastomer composition, the quantity of TFDAIC required to cause a certain degree of gel formation is greater than the quantity of HFTAIC required to produce that same degree of gel formation in a polymer otherwise equivalent. Depending on the gel content desired, a preferred minimum quantity of HFTAIC is about 0.25% by weight. Depending on economics and the sacrifice of vulcanizate properties that can be tolerated, a preferred maximum quantity of HFTAIC is about 0.5% by weight. For an optimum balance between processability, cost and vulcanizate properties, the most preferred range of HFTAIC is about 0.35–0.45% by weight.

In preparing the gelled fluoroelastomer of the present invention it is preferred that the reaction mixture of monomer components also contains a free-radical initiator, and the copolymer-forming reaction is carried out as a free-radical emulsion polymerization reaction. Among the most useful free-radical initiators to use in such a reaction are ammonium persulfate, sodium persulfate, potassium persulfate, or a mixture of two or more such compounds. Also useful are other water-soluble inorganic peroxide compounds, for example, sodium, potassium and ammonium perphosphates, perborates, and percarbonates. The initiator can be used in combination with a reducing agent such as sodium, potassium, or ammonium sulfite, bisulfite, metabisulfite, hyposulfite, or phosphite, or in combination with a ferrous or a cuprous salt, or a salt of other easily oxidized metal compounds. Known organic free-radical initiators can also be used, preferably in combination with a suitable surfactant such as sodium lauryl sulfate or ammonium perfluorooctanoate. The surfactant can be selected from those known to be useful in the manufacture of fluoropolymers. A suitable known chain transfer agent can also be present during the emulsion polymerization reaction, but in many cases this is not preferred.

After completion of the preferred emulsion polymerization reaction, the copolymer can be isolated from the resulting polymer latex by known methods, for example by coagulation by adding an electrolyte or by freezing, followed by centrifuging or filtering and then drying the copolymer.

During preparation of the copolymer, the reaction mixture is preferably heated in a reactor which has been flushed with an inert gas at about 50°–130° C. under superatmospheric pressure, for example under a pressure of about 7–140 kg/cm$^2$, preferably about 35–105 kg/cm$^2$. In some of the most useful procedures, the polymerization is carried out as a continuous process and the reaction mixture has an average residence time in the reactor of about 5 to 30 minutes in some cases and up to 2 or 3 hours in others. Residence time can be calculated by dividing the reactor volume by the volume of latex produced per hour.

The fluoroelastomer blends of the present invention can be prepared by mixing a latex of HFTAIC or TFDAIC gelled fluoroelastomer with a latex of a non-crosslinked fluoroelastomer, and isolating the blended fluoroelastomer of the latex mixture. The gel content of the fluoroelastomer blend can be from 10–90%, preferably will be from 10–75%, more preferably from 25–75%, and most preferably will be from 30–55%. In peroxide-curable fluoroelastomer blends, such as those derived from TFE, VF$_2$, HFP and BTFB, it is most preferred that the gel content be about 50%. In other fluoroelastomer blends it is most preferred that the gel content be about 35%. It should be understood that one can achieve the desired gel content of the blend by adjusting the quantity of gel component in the blend, by adjusting the quantity of gel component in the gel component in the blend, or by a combination of these. The monomer composition of the gelled fluoroelastomer may be the same or different than the monomer composition of the non-crosslinked fluoroelastomer.

The latex mixture itself can be considered as a useful article of commerce since it can be shipped to the plants of customers who will blend it with various additives or subject it to certain processes which will convert it into final products such as coating compositions, extruded articles or molded or laminated products.

The fluoroelastomer blends of the present invention can also be prepared by mixing the two different fluoroelastomers in the form of solid particles (e.g., wet or dry crumb), on a high shear mixing device (e.g. Banbury, extruder or rubber mill), or by mixing while they are in the form of a dispersion in an organic liquid.

Before the fluoroelastomer blends of this invention are formed into shaped structures by extrusion or molding it is usually preferred to mix them with various additives which include metal oxides, cross-linking agents, unsaturated coagents, accelerators, stabilizers, pigments, pore-forming agents and plasticizers. Such compounding and subsequent vulcanization can be achieved by methods and with materials such as are generally known in the arts relating to fluoroelastomers, which techniques and materials are typified by those disclosed in U.S. Pat. Nos. 2,968,649, 3,051,677, 3,235,537, 3,851,018, 4,035,565 and 4,115,481 and U.K. Pat. No. 1,496,084.

The fluoroelastomer blends of the present invention have superior processing properties, particularly with respect to extrusion and milling. Such blends can be made into extrudable fluoroelastomer compositions. Extrusion can be carried out in an extruder of the type commonly used for processing fluoroelastomers. The milling performance of the fluoroelastomer blends of the present invention is markedly improved as compared with the performance of non-crosslinked fluoroelastomers.

The following examples identify various specific fluoroelastomers of the present invention and methods of making them. In addition, certain of the examples compare processing properties of the fluoroelastomer blends of the present invention with the same properties of similar fluoroelastomers outside the scope of the present invention. In these examples, all parts and percentages are by weight unless stated otherwise.

EXAMPLE 1

Synthesis of HFTAIC by process of equations (1), (2) and (4).

To a 1000 cm³ shaker bomb was added 400 ml $CF_2Br_2$ (900 g, 4.29 mol) and 4 g (0.02 mol) benzoyl peroxide. The bomb was closed and evacuated at $-60°$ C. A 40 g (1.43 mol) sample of ethylene was then introduced and the bomb was heated to 80° C. for 4 hours. At the end of this period, the bomb was cooled to room temperature and vented to atmospheric pressure. A total of five runs were carried out in this manner and the combined product obtained after removal of excess $CF_2Br_2$ was fractionated in a spinning band column to give 1250 g $CH_2BrCH_2CF_2Br$, b.p. 120° C., $n_D^{20}=1.4450$, d=2.0353. This represents a 79% yield based on 35% conversion.

To a 1 liter flask equipped with a stirrer, thermometer, $N_2$ inlet and condenser in series with 2 dry ice/acetone traps and a funnel was added 220 g (5.5 mol) NaOH, 150 g of $H_2O$ and 2-3 g Aliquat 336 (trioctoyl methyl ammonium chloride, available from General Mills Chemicals, Inc., Minneapolis, Minn.). The solution was warmed to 90° C. and 500 g (2.10 mol) 1,1-difluoro-1,3-dibromopropane was added dropwise with a $N_2$ flow through the reactor and traps. The material in the traps was fractionally distilled to give 178 g $CH_2$=$CHCF_2Br$, b.p. 40° C., $n_D^{20}=1.3773$ and 65 g $BrCF_2CH_2CH_2Br$. Yield: 62%; conversion: 87%.

To a 400 cm³ stainless steel shaker bomb was added 43 g (0.22 mol) trisodium cyanurate and 120 g (0.76 mol) $CH_2$=$CHCF_2Br$ dissolved in 250 ml DMAc. The bomb was closed and evacuated at $-75°$ C. The contents were heated to 60° C. They were maintained at this temperature for 6 hours. The bomb was cooled to room temperature and vented to atmospheric pressure. A total of seven such runs yielded about 500 g of crude product which was fractionally distilled to yield 295 g HFTAIC, b.p. 135° C./1.0 mm, $n_D^{20}=1.4557$.

Analysis: Calculated for $C_{12}H_9F_6N_3O_3$, C: 40.3%, H: 2.5%, F: 31.9%, N: 11.8%. Found: C: 40.8%, H: 2.5%, F: 32.0%, N: 11.8%.

EXAMPLE 2

Synthesis of HFTAIC by process of equation (5)

To 550 ml dimethylacetamide in a stirred flask with an air-cooled reflux condenser there was added 64.4 g (1.15 mol) calcium oxide, 40.3 g (1.0 mol) magnesium oxide, 45 g (0.35 mol) cyanuric acid. To this heterogeneous mixture there was then added one-fourth (63.4 g) of a total of 253.5 g (3.195 mol) dibromodifluoropropane to be added. The temperature was raised to 90° C. over one-half hour. As the exothermic reaction progressed heat was removed, but the temperature was allowed to rise to about 125° C., and the remaining dibromide was then added over about 35 minutes at a rate to maintain the temperature at about 130° C. The reaction mixture was stirred and maintained at about 130° C. for an additional 6 hours, allowed to stand overnight, and treated in portions with 4 N HCl (total 450 ml) and water (total 225 ml) until $CO_2$ evolution ceased, all solids dissolved, and an oil separated. The oil (118.5 g) was obtained, analyzing 75.6% HFTAIC and 12% DMAc, for a yield 71.7% of theoretical, based on cyanuric acid.

EXAMPLE 3

Synthesis of HFTAIC by process of equation (5')

In a manner generally similar to that of Example 2, 19.5 g (~0.10 mol) trisodium cyanurate and 11.2 g (0.20 mol) calcium oxide were slurred in 110 ml dimethyl acetamide, and reacted with 71.1 g (0.30 mol) dibromodifluoropropane, half of which was added at room temperature, the remainder being added after heating to about 80° C. On further heating to 110° C., the temperature rose to 150° C. over 10 minutes as the result of a brief exothermic reaction. The mixture was stirred an additional three hours at 120° C., cooled, and treated with 200 ml 4 N HCl and 100 ml $H_2O$. An oil (29.0 g) separated, which contained 23 g hexafluorotriallylisocyanurate by analysis, for a yield 65% of the theoretical amount.

EXAMPLE 4

Preparation of HFTAIC gelled fluoroelastomer

A curable fluoroelastomer of this invention was prepared by a continuous process composed of the following steps:

(1) Gaseous monomers were fed continuously to a 2 liter stainless steel autoclave while the stirrer of the reactor was operated at 885 rpm for thorough mixing of the reactor contents. The contents of the reactor were heated at 105° C. under a pressure of 6.31 MPa so that the reaction mixture formed in operation (2) below would undergo an emulsion polymerization reaction as it passed through the reactor. The reactor residence time was about 15 minutes based on a water flow of about 8 liters/hr. The monomers used and the feed rate of each are shown in Table I below;

(2) During each hour of operation (1) a solution composed of 6.8 g ammonium persulfate and 0.8 g sodium hydroxide in 4 liters of water was continuously fed to the reactor through a first metering pump, a solution of 2.0 g of sodium sulfite in 4 liters of water was continuously fed to the reactor through a second metering pump, and a solution of 19 g hexafluorotriallylsiocyanurate in 28.5 g of t-butyl alcohol was continuously fed to the reactor through a third metering pump.

(3) The resulting copolymer latex was continuously removed from the reactor by passing it first through a back pressure regulating valve set to maintain the desired reactor pressure of 6.31 MPa, and then through a sealed container from which the unreacted monomers were led to a gas chromatograph where the composition of the stream was determined. The off gas rate for each monomer and the amount of each monomer incorporated into the polymer are also shown in Table I.

(4) After discarding the latex obtained during the first four residence times, the desired quantity of latex having a solids content of about 19% was collected.

(5) The resulting copolymer was then isolated from the latex by gradually adding a 4% aqueous solution of potassium aluminum sulfate until the polymer was coagulated, washing the copolymer particles with water, removing the water by filtration, and then drying the copolymer obtained in a circulating air oven at about 65° C. to a moisture content of less than 1%.

TABLE I

|   | Feed g/hr | Off Gas g/hr | Incorporated in polymer g/hr | wt. % | Mole % |
|---|---|---|---|---|---|
| TFE | 475 | 5 | 470 | 25.2 | 21.9 |
| VF$_2$ | 860 | 15 | 845 | 45.3 | 61.5 |
| HFP | 660 | 129 | 531 | 28.5 | 16.5 |
| HFTAIC | 19 | — | 19 | 1.0 | 0.16 |
|   | 2014 | 149 | 1865 |   |   |

The gel content of this polymer was determined to be about 97.0%.

EXAMPLE 5

Preparation of HFTAIC gelled fluoroelastomer

A gelled terpolymer of TFE, VF$_2$, HFP and HFTAIC was prepared as described in Example 4 above at a temperature of 105° C. and a pressure of 6.31 MPa with a latex residence time of 15 min. Monomers were fed to the reactor at the following rates: TFE: 475 g/h; VF$_2$: 860 g/h; HFP: 660 g/h and HFTAIC: 38.2 g/h. Also present in the latex were 0.51 g ammonium persulfate/100 g polymer produced, 0.12 sodium sulfite/100 g polymer produced and 0.06 g sodium hydroxide/100 g polymer produced. Conversion of monomers to polymers was 65.9%. The dried copolymer comprised 30.6 wt.% TFE, 53.1 wt.% VF$_2$, 13.4 wt.% HFP and 2.8 wt. % HFTAIC. It had a gel content of 98.0%.

EXAMPLE 6

Preparation of HFTAIC gelled fluoroelastomer

A curable fluoroelastomer of this invention was prepared by the process described in Example 3 except that the gaseous monomers were fed at rates as shown in Table II below and liquid feeds (per hour) comprised (1) 5.83 g ammonium persulfate and 1.67 g sodium hydroxide in 3 liters water, (2) 0.72 grams sodium sulfite in 3 liters water, and (3) 18.6 g HFTAIC in sufficient t-butyl alcohol to obtain a volume of 50 ml.

TABLE II

|   | Feed g/hr | Off Gas g/hr | Incorporated in polymer g/hr | wt. % | Mole % |
|---|---|---|---|---|---|
| VF$_2$ | 1130 | 72 | 1058 | 64.3 | 81.2 |
| HFP | 870 | 302 | 568 | 34.5 | 18.6 |
| HFTAIC | 18.6 | — | 18.6 | 1.1 | 0.26 |
|   | 2018.6 | 374 | 1644.6 |   |   |

The gel content of this polymer was determined to be about 96.6%.

EXAMPLE 7

Preparation of HFTAIC gelled fluoroelastomer

A curable fluoroelastomer of this invention was prepared by the process described in Example 6 except that the feed of HFTAIC was 9.28 g in 25 ml total solution, the results obtained are summarized in Table III.

TABLE III

|   | Feed g/hr | Off Gas g/hr | Incorporated in polymer g/hr | wt. % | Mole % |
|---|---|---|---|---|---|
| VF$_2$ | 1130 | 32 | 1098 | 60.3 | 78.2 |
| HFP | 870 | 156 | 714 | 39.2 | 21.7 |
| HFTAIC | 9.26 | — | 9.26 | 0.51 | 0.12 |
|   | 2009.26 | 188 | 1821.26 |   |   |

The gel content of this polymer was determined to be about 92.9%.

EXAMPLE 8

Preparation of HFTAIC gelled fluoroelastomer

A curable fluoroelastomer of this invention was prepared by continuous emulsion polymerization in a stirred 2 liter autoclave maintained at 115° C., 6.31 MPa, with a latex residence time of 20 minutes in the reactor, using as the free radical initiator 0.3 grams ammonium persulfate per 100 g polymer produced. In addition, 0.05 grams sodium hydroxide per 100 g polymer produced and 0.05 grams ammonium perfluorooctanoate per 100 g of polymer produced was also present. Monomers were fed to the reactor at the following rates: 493 g/h tetrafluoroethylene (TFE), 913 g/h vinylidene fluoride (VF$_2$), 691 g/h hexafluoropropylene (HFP), 26 g/h 4-bromo-3,3,4,4-tetrafluorobutene-1 (BTFB) and 7.33 g/h hexafluorotriallylisocyanurate (HFTAIC). Conversion of total monomers to polymer was 87.6%. The latex was coagulated by addition of potassium aluminum sulfate solution, the resulting crumb then being washed several times and dried at about 60° C. in a circulating air oven. The dried copolymer comprised 25.7 wt.% TFE, 46.9 wt.% VF$_2$, 25.6 wt.% HFP, 1.37 wt.% BTFB and 0.39 wt.% HFTAIC. The polymer had a gel content of 89.1%, as determined by a method based on high speed centrifugation of a dilute solution of the polymer in ethyl methyl ketone.

EXAMPLE 9

Preparation of HFTAIC gelled fluoroelastomer

A curable fluoroelastomer of this invention was prepared in a manner similar to that described in Example 8 above, in the presence of 0.3 g ammonium persulfate/100 g polymer produced using monomer flows per hour of 486 g TFE, 901 g VF$_2$, 682 g HFP, 27.6 g BTFB and 1.38 g HFTAIC. The residence time in the reactor was 20 minutes and the reaction temperature was 105° C. The resulting product contained 25.4 wt.% TFE, 45.6 wt.% VF$_2$, 26.5 wt.% HFP, 1.46 wt.% BTFB and 0.073 wt.% HFTAIC. It had a gel content of 58% and a Mooney viscosity [ML-10 (100° C.)] = 170. This fluoroelastomer was designated Sample B.

EXAMPLE 10

Preparation and properties of fluoroelastomer blends

A gelled fluoroelastomer prepared as described in Example 8, above, was blended with an essentially gel-free copolymer similarly prepared using monomer flows per hour of 615 g TFE, 1118 g VF$_2$, 852 g HFP and 39.5 g BTFB. Also present in the latex of the gel-free polymer were 0.39 g ammonium persulfate per 100 g polymer produced and 0.09 g sodium hydroxide per 100 g polymer produced. Conversion of total monomers to gel-free polymer was 875. Product composition: 26.1 wt.% TFE, 46.9 wt.% VF$_2$, 25.2 wt.% HFP and 1.73 wt.% BTFB. The gel-free polymer had inherent viscosity 1.39 and Mooney viscosity [ML-10 (121° C.)] = 80.

A 640 g sample of the gelled polymer was mill-mixed with a 360 g sample of the sol (gel-free) polymer to give a blend of the present invention having a gel content of 58%. This blend was designated as Sample A.

A control gelled fluoroelastomer was prepared in the manner described in Example 9 above. Composition of the isolated polymer was approximately 25 wt.% TFE, 45 wt.% VF$_2$, 30 wt.% HFP and 0.8 wt.% BTFE (bromotrifluoroethylene). This polymer was mill-blended with a 60:40 VF$_2$/HFP copolymer in a ratio of 9:1. The gel content of the resultant control blend was 58%. The Mooney viscosity was [ML-10(121° C.)]-90. The resultant blend is substantially as described by Finlay and Omura in U.S. Patent 4,115,481 cited and discussed above. This control blend was designated as Sample C.

A control sol (non-gelled) polymer composed of 25.0 wt.% TFE, 45.5 wt.% VF$_2$, 27.8 wt.% HFP and 1.72 wt% BTFB was prepared as generally described above at 105° C., residence time was 20 minutes, in the presence of 0.5 grams ammonium persulfate/100 g polymer produced. The product had Mooney viscosity [ML-10(121° C.)] = 78 and was designated as Sample D.

The gelled fluoroelastomers of the present invention as described in detail in Examples 8 and 9 (i.e., Samples A and B), above, and the control blend and control sol polymers described immediately above (i.e., Samples C and D), were compounded according to the following recipe:

| | |
|---|---|
| Polymer | 100 parts |
| Carbon Black | 30 parts |
| Litharge (PbO) | 3 parts |
| Diak #7 (Triallylisocyanurate) | 2.5 parts |
| Luperco 130XL (45% 2,5-dimethyl-2,5-di-t-butylperoxyhexene-3, 55% inert filler | 2.5 parts |
| VPA #2 (Rice bran wax) | 2.0 parts |

Samples A, B, C and D, compounded as above, were extruded through a 2 inch Royle Extruder, equipped with a 3/8 inch cord die, at the following conditions: barrel 60° C.; head, 77° C.; feed, 46° C.; die, 100° C. (center); screw 60° C., 30 rpm. Results are shown in Table IV.

TABLE IV

| Polymer | Extrusion Rate (g/min) | Die Swell (g/mm) |
|---|---|---|
| A | 200 | 0.202 |
| B | " | 0.195 |
| C | " | 0.226 |
| D | " | 0.289 |
| A | 300 | 0.204 |
| B | " | 0.200 |
| C | " | 0.228 |
| D | " | 0.309 |

Samples A, B, C and D, compounded as above, were cured at 170° C. for 30 minutes and post-cured at 232° C. for 24 hours. Physical properties of the vulcanizates were determined by the procedures of ASTM 412 and D-395 and were as noted in Table V.

TABLE V

| | Sample | | | |
|---|---|---|---|---|
| | A | B | C | D |
| Room Temp. | | | | |
| T$_B$ (MPa) | 14.1 | 13.8 | 10.0 | 17.6 |
| M$_{100}$ (MPa) | 7.9 | 6.2 | 6.5 | 5.2 |
| E$_B$ (%) | 185 | 180 | 165 | 240 |
| Set at Break | 4 | 6 | 4 | 5 |
| Heat Aged 70h/275° C. | | | | |
| T$_B$ (MPa) | 12.1 | 9.7 | 8.3 | 12.4 |
| M$_{100}$ (MPa) | 5.5 | 3.1 | 4.6 | 3.1 |
| E$_B$ (%) | 185 | 300 | 180 | 300 |
| Set at break | 7 | 10 | 6 | 9 |
| Compression set (70h/204° C.) | 34 | 41 | 37 | 30 |

EXAMPLE 11

Preparation and properties of fluoroelastomer blends

Three fluoroelastomers having compositions as shown in Table VI were prepared as described above.

TABLE VI

| Sample | Blend Components (%) | TFE (wt. %) | VF$_2$ (wt. %) | HFP (wt. %) | BTFB (wt. %) | HFTAIC (wt. %) | BTFE (wt. %) |
|---|---|---|---|---|---|---|---|
| E | 90 | 25 | 45 | 30 | — | — | 0.8 |
| E | 10 | — | 60 | 40 | — | — | — |
| F | 62.5 | 26.1 | 46.6 | 25.5 | 1.44 | 0.41 | — |
| F | 37.5 | 25.6 | 45.4 | 27.3 | 1.70 | — | — |
| G | 100 | 25.6 | 45.4 | 27.3 | 1.70 | — | — |

Sample E: % gel in blend: 58%, ML-10(121° C.) = 106
Sample F: % gel in blend: 54%
Sample G: ML-10(121° C.) = 92

These samples were compounded using the recipe in Example 10 above. Instron capillary rheometer extrusions at 70° C. afforded the following comparisons.

TABLE VII

| Sample | Extrusion Rate (mm³/s) | Die Diam (mm) | Extrusion Force (MPa) | Extrudate Diam (mm) |
|---|---|---|---|---|
| E | 3.01 | 3.18 | 21.5 | 3.51[1] |
| F | 3.01 | 3.18 | 18.7 | 3.23[1] |
| G | 3.01 | 3.18 | 17.2 | 3.58[1] |
| E | 30.1 | 3.18 | 33.7 | 3.40[2] |
| F | 30.1 | 3.18 | 25.6 | 3.25[2] |
| G | 30.1 | 3.18 | 23.1 | 3.51[2] |
| E | 150.7 | 3.18 | 43.7 | 3.40[3] |
| F | 150.7 | 3.18 | 37.5 | 3.20[3] |
| G | 150.7 | 3.18 | 31.2 | 3.48[3] |

[1] torn surface
[2] rough surface
[3] dull surface - no irregularities at 10× magnification The above data show that at identical extrusion rates, the diameter of Sample F extrudate more nearly conformed to the die diameter than did the diameters of either Sample E or Sample G extrudates.

Similar results were obtained at 120° C. In addition, the surface of Sample F extrudate was superior to that of Samples E or G when the extrusion was carried out at 120° C., as summarized in Table VIII.

TABLE VIII

| Sample | Extrusion Rate (mm³/s) | Die Diam (mm) | Extrusion Force (MPa) | Extrudate Diam (mm) |
|---|---|---|---|---|
| E | 3.01 | 3.18 | 11.2 | 3.30[2] |
| F | 3.01 | 3.18 | 8.4 | 3.15[1] |
| G | 3.01 | 3.18 | 10.0 | 3.40[2] |
| E | 30.1 | 3.18 | 14.4 | 3.30[1] |
| F | 30.1 | 3.18 | 9.4 | 3.23[1] |
| G | 30.1 | 3.18 | 16.2 | 3.66[3] |
| E | 150.7 | 3.18 | 21.2 | 3.40[4] |
| F | 150.7 | 3.18 | 20.6 | 3.28[3] |
| G | 150.7 | 3.18 | 21.9 | 3.63[3] |

[1] smooth and shiny surface
[2] torn surface
[3] rough surface 10× magnification
[4] cracked surface Further extrusion of Sample F and G stocks through a 2" Royle Extruder with a 9.5 mm cord die at a rate of approximately 400 g/min. afforded the following die swell measurements: 1:900 g/mm for the blend and 3.46 g/mm for the non-crosslinked rubber stock.

Samples E, F and G, as compounded, were cured as described in Example 10. Physical properties after cure, measured as described in Example 10, are as shown in Table IX.

TABLE IX

| Sample | E | F | G |
|---|---|---|---|
| Properites at Room Temp. | | | |
| $T_B$ (MPa) | 13.1 | 18.0 | 15.9 |
| $M_{100}$ (MPa) | 6.6 | 9.0 | 7.2 |
| $E_B$ (%) | 160 | 160 | 185 |
| Set at Break | 4 | 4 | 4 |
| Compression Set | 29 | 27 | 30 |

EXAMPLE 12

Preparation and properties of fluoroelastomer blends

The gelled fluoroelastomer of Example 5 was mixed on a rubber mill with an equal weight of an all-sol TFE/VF$_2$/HFP copolymer comprising 25 wt.% TFE, 45 wt.% VF$_2$ and 30 wt.% HFP. Samples of the gel-sol blend and the sol polymer were compounded according to the following recipe (in parts by weight).

| | |
|---|---|
| Polymer | 100 |
| Carbon Black | 30 |
| Magnesium Oxide | 15 |
| N,N'-dicinnamylidene-1,6-hexane-diamine | 3 |

Properties of the samples are shown in Table X.

TABLE X

| | Blend | Sol |
|---|---|---|
| Mooney Viscosity [ML-10(121° C.)] | 100 | 64 |
| Properties of Stocks Cured 24h/232° C. | | |
| Compression Set[1] (70h/232° C.) | 79 | 83 |
| Properties at 150° C. | | |
| $T_B$ (MPa)[2] | 4.0 | 3.5 |
| $E_B$ (%)[2] | 40 | 112 |
| Set at break[2] | 1 | 2 |
| Properties at 20° C. | | |
| $T_B$ (MPa)[2] | 12.4 | 16.2 |
| $M_{100}$ (MPa)[2] | — | 5.0 |
| $E_B$ (%)[2] | 70 | 230 |
| Hardness[3] | 92 | 76 |

[1] ASTM D-395
[2] ASTM 412
[3] ASTM D-2240

Instron capillary rheometer extrusions at 70° C. gave the following data.

TABLE XI

| Sample | Extrusion Rate (mm³/s) | Die Diam (mm) | Extrusion Force (MPa) | Extrudate Diam (mm) |
|---|---|---|---|---|
| Sol | 8.5 | 1.27 | 31.2 | 1.37[1] |
| Blend | 8.5 | 1.27 | 39.3 | 1.27[1] |
| Sol | 2115 | 1.27 | 143.5 | 1.40[2] |
| Blend | 423 | 1.27 | 152.9 | 1.30[1] |

[1] Surface rough
[2] Tears, jagged surface

Similar results in die swell with improved surface properties are seen when the extrusion was run at 120° C.

TABLE XII

| Sample | Extrusion Rate (mm³/s) | Die Diam (mm) | Extrusion Force (MPa) | Extrudate Diam (mm) |
|---|---|---|---|---|
| Sol | 8.5 | 1.27 | 32.5 | 1.37[1] |
| Blend | 8.5 | 1.27 | 32.5 | 1.30[2] |
| Sol | 8460 | 1.27 | 88.9* | 1.47[1] |
| Blend | 8460 | 1.27 | 146.6* | 1.32[2] |

*Force was read after only 1.5 min from start of extrusion since fast extrusion depleted sample from reservoir. Other data taken at 4.0 min after start.
[1] Irregularities visible at 10× magnification.
[2] Smooth at 10× magnification. Surface Rating: excellent.

EXAMPLE 13

Preparation and properties of fluoroelastomer blends

A gel-sol blend was prepared in a manner similar to that described in Example 12 above. The following conditions were used for preparation of the gel.

| | |
|---|---|
| Reaction Temp (°C.) | 105 |
| Pressure (MPa) | 6.31 |
| Residence time (min) | 15 |
| g NH$_4$S$_2$O$_8$/100 g polymer | 0.36 |
| g NaSO$_3$/100 g polymer | 0.107 |
| g NaOH/100 g polymer | 0.043 |
| TFE (g/h) | 475 |
| VF$_2$ (g/h) | 860 |
| HFP (g/h) | 660 |

| | -continued | |
|---|---|---|
| HFTAIC (g/h) | | 19 |
| Conversion (%) | | 92.6 |

The product contained 25.2 wt. % TFE, 45.3 wt. % VF$_2$, 28.4 wt. % HFP and 1.0 wt. % HFTAIC. % Gel=96%. It was mill-mixed with an equal portion of the sol polymer used in Example 12.

Samples of the gel-sol blend and the sol were compounded using the recipe in Example 12. Physical properties were measured as described in Example 12 and are shown in Table XIII.

TABLE XIII

| | Blend | Sol |
|---|---|---|
| Mooney Viscosity [ML-10 (121° C.)] | 93 | 64 |
| Compression Set (70h/232° C.) | 77 | 83 |
| Properties at 150° C. | | |
| T$_B$ (MPa) | 3.5 | 3.5 |
| E$_B$ (%) | 45 | 112 |
| Set at Break | 1 | 2 |
| Properties at 20° C. | | |
| T$_B$ (MPa) | 13.1 | 16.2 |
| M$_{100}$ (MPa) | 12.9 | 5.0 |
| E$_B$ (%) | 105 | 230 |
| Hardness | 88 | 76 |

Instron rheometer extrusions at 70° C. showed the following comparisons.

TABLE XIV

| Sample | Extrusion Rate (mm$^3$/s) | Die Diam (mm) | Extrusion Force (MPa) | Extrudate Diam (mm) |
|---|---|---|---|---|
| Sol | 8.5 | 1.27 | 31.2 | 1.37[1] |
| Blend | 8.5 | 1.27 | 35.6 | 1.27[2] |
| Sol | 2115 | 1.27 | 143.5 | 1.40[3] |
| Blend | 8460 | 1.27 | 162.2 | 1.30[4] |

[1] Surface rough
[2] Smooth at 10× magnification. Surface rating: excellent
[3] Tears, jagged surface
[4] Irregularities visible only at 10× magnification.

Similar results were obtained at 120° C. as summarized in Table XV.

TABLE XV

| Sample | Extrusion Rate (mm$^3$/s) | Die Diam (mm) | Extrusion Force (MPa) | Extrudate Diam (mm) |
|---|---|---|---|---|
| Sol | 8.5 | 1.27 | 32.5 | 1.37[1] |
| Blend | 8.5 | 1.27 | 33.1 | 1.27[2] |
| Sol | 8460 | 1.27 | 88.9 | 1.47[1] |
| Blend | 8460 | 1.27 | 137.5 | 1.32[2] |

[1] Irregularities visible at 10× magnification
[2] Smooth at 10× magnification. Surface rating: excellent

EXAMPLE 14

Preparation and properties of fluoroelastomer blends

A terpolymer was prepared as described in Example 4 above at a temperature of 115° C. and a pressure of 6.31 MPa with a latex residence time of 15 min.

Monomers were fed to the reactor at the following rates: VF$_2$, 1380 g/hr; HFP, 1020 g/hr; HFTAIC, 5.15 g/hr. Also fed to the latex were ammonium persulfate, 6.0 g/hr; sodium hydroxide, 0.8 g/hr; and "Zonyl" UR long chain fluorinated surfactant, 7.0 g/hr. Conversion of monomers to polymer was 93.7%, the dried copolymer comprising 60.2 wt. % VF$_2$, 39.6 wt. % HFP, and 0.22 wt. % HFTAIC. It had a microgel content of 79.0% and a Mooney viscosity ML-10=104 at 121° C.

This terpolymer was formulated on a rubber mill as follows:

| | A | B | C | D |
|---|---|---|---|---|
| Precompounded Sol Fluoroelastomer Control* | 100 | — | — | — |
| Gelled terpolymer described above | — | 25 | 37.5 | 50 |
| Sol control without curatives | — | 75 | 63.5 | 50 |
| Benzyltriphenyl phosphonium chloride | — | 0.5 | 0.5 | 0.5 |
| Bisphenol AF | — | 1.2 | 1.6 | 2.0 |
| Ca(OH)$_2$ | 6 | 6 | 6 | 6 |
| MT black (carbon black) | 30 | 30 | 30 | 30 |
| Magnesium oxide | 3 | 3 | 3 | 3 |

*A sol copolymer of 60 wt % VF$_2$ and 40 wt % HFP compounded with 0.55 parts benzyl triphenyl phosphonium chloride and 2.0 parts bisphenol AF Properties of Samples A-D, measured as described in Example 12, are shown in Table XVI.

TABLE XVI

| | Sample | | | |
|---|---|---|---|---|
| | A (Sol) | B | C | D |
| Mooney Viscositiy [ML-10(121° C.)] | 37 | 42 | 45 | 49 |
| Properties of Stocks Cured 24h/232° C. | | | | |
| Compression Set (70h/232° C.) | | | | |
| Pellets | 39 | 52 | 39 | 35 |
| "O" Rings | 33 | 46 | 36 | 31 |
| Properties at 20° C. | | | | |
| T$_B$ (MPa) | 12.4 | 11.6 | 13.8 | 12.6 |
| E$_B$ (%) | 170 | 240 | 200 | 190 |
| M$_{100}$ (MPa) | 6.2 | 3.8 | 5.9 | 6.9 |
| Permanent Set[1] | 5 | 5 | 6 | 6 |
| Heat Aged (7d/275° C.) | | | | |
| T$_B$ (MPa) | 12.4 | 10.7 | 12.4 | 12.4 |
| E$_B$ (%) | 170 | 290 | 220 | 200 |
| M$_{100}$ (MPa) | 6.7 | 3.8 | 5.5 | 6.4 |
| Permanent Set | 6 | 8 | 6 | 8 |

[1] ASTM 412

Samples A-D were extruded in a Monsanto Processability Tester (a type of capillary rheometer). A Garvey Die (a die with 180° entrance angle having an irregularly shaped cross section and producing an extrudate with sharp edges) was used. Temperatures of 93° C. and 132° C. and piston speeds of 0.254 cm/min and 2.29 cm/min were used.

The extrudates were cut into equal lengths after cooling and were then weighed to determine the relative die swell (Barus effect). The greater the weight of the extrudate per unit length, the larger was its cross section and hence its relative die swell. Data obtained is summarized in Tables XVII and XVIII and in FIGS. 1 and 3. Some of the die swell data presented below is the average of two replications.

TABLE XVII

| Blend | Wt % HFTAIC in Gel | Amount of Gel Component in Blend (%) | Piston Speed (cm/min) | Extrusion Temp = 93° C. Relative Die Swell (g) |
|---|---|---|---|---|
| A | 0.22 | 0 | 0.254 | 2.58 |
| B | 0.22 | 25 | 0.254 | 2.15 |
| C | 0.22 | 37.5 | 0.254 | 1.98 |
| D | 0.22 | 50 | 0.254 | 1.89 |
| A | 0.22 | 0 | 2.29 | 2.56 |
| B | 0.22 | 25 | 2.29 | 2.22 |
| C | 0.22 | 37.5 | 2.29 | 2.08 |

TABLE XVII-continued

| Blend | Wt % HFTAIC in Gel | Amount of Gel Component in Blend (%) | Piston Speed (cm/min) | Extrusion Temp = 93° C.* Relative Die Swell (g) |
|---|---|---|---|---|
| D | 0.22 | 50 | 2.29 | 2.00 |

*At this low extrusion temperature all samples showed some tearing at the edges, making the errors in measuring relative die swell somewhat greater than at higher temperatures where extrudates were smoother.

XVIII

| Blend | Wt % HFTAIC in Gel | Amount of Gel Component in Blend (%) | Piston Speed (cm/min) | Extrusion Temp = 132° C. Relative Die Swell (g) |
|---|---|---|---|---|
| A | 0.22 | 0 | 0.254 | 2.00 |
| B | 0.22 | 25 | 0.254 | 2.17 |
| C | 0.22 | 37.5 | 0.254 | 1.83 |
| D | 0.22 | 50 | 0.254 | 1.82 |
| A | 0.22 | 0 | 2.29 | 2.51 |
| B | 0.22 | 25 | 2.29 | 2.18 |
| C | 0.22 | 37.5 | 2.29 | 1.93 |
| C | 0.22 | 50 | 2.29 | 1.85 |

The data summarized above demonstrates that in all cases except one (Table XVIII, 25% gel component, in blend, piston speed=0.254), the blend gives a product which exhibits less die swell than the sol polymer.

EXAMPLE 15

Preparation and properties of fluoroelastomer blends

A terpolymer was prepared as described in Example 4 above at a temperature of 115° C. and a pressure of 6.31 MPa with a latex residence time of 15 min.

Monomers were fed to the reactor at the following rates: $VF_2$, 1380 g/hr; HFP, 1020 g/hr; HFTAIC, 10.3 g/hr. Also fed to the latex were ammonium persulfate, 6.0 g/hr; sodium hydroxide, 0.8 g/hr; and "Zonyl" UR long chain fluorinated surfactant, 7.0 g/hr. The dried copolymer comprised 61.5 wt % $VF_2$, 38.0 wt % HFP, and 0.45 wt % HFTAIC. It had a microgel content of 90.8 and a Mooney viscosity ML-10=116 at 121° C.

This terpolymer was formulated on a rubber mill as follows:

|  | A | B | C | D |
|---|---|---|---|---|
| Precompounded Sol Fluoroelastomer Control* | 100 | — | — | — |
| Gelled terpolymer described above | — | 25 | 37.5 | 50 |
| Sol control without curatives | — | 75 | 62.5 | 50 |
| Benzyltriphenyl phosphonium chloride | — | 0.5 | 0.575 | 0.5 |
| Bisphenol AF | — | 1.6 | 1.6 | 1.6 |
| Ca(OH)$_2$ | 6 | 6 | 6 | 6 |
| MT black (carbon black) | 30 | 30 | 30 | 30 |
| Magnesium oxide | 3 | 3 | 3 | 3 |

*A sol copolymer of 60 wt % $VF_2$ and 40 wt % HFP compounded with 0.55 parts benzyl triphenyl phosphonium chloride and 2.0 parts bisphenol AF.

Properties of Samples A-D, measured as described in Example 12, are shown in Table XIX.

TABLE XIX

| | Samples | | | |
|---|---|---|---|---|
| | A (Sol) | B | C | D |
| Properties of Stocks Cured 24 h/232° C. | | | | |
| Compression Set[1] (70 h/232° C.) | | | | |
| Pellets | 41 | 41 | 39 | 37 |
| "O" Rings | 33 | 37 | 34 | 34 |
| Properties at 20° C. | | | | |
| $T_B$ (MPa) | 13.8 | 12.6 | 13.4 | 12.9 |
| $E_B$ (%) | 180 | 215 | 205 | 190 |
| $M_{100}$ (MPa) | 7.2 | 5.7 | 6.6 | 6.9 |
| Permanent Set[2] | 5 | 5 | 6 | 5 |
| Heat Aged (7 d/275° C.) | | | | |
| $T_B$ (MPa) | 11.7 | 8.6 | 9.3 | 9.1 |
| $E_B$ (%) | 180 | 215 | 205 | 190 |
| $M_{100}$ (MPa) | 6.6 | 4.1 | 4.8 | 5.2 |
| Permanent Set[2] | 6 | 7 | 7 | 7 |

[1]ASTM D-395
[2]ASTM 412

Samples A-D were extruded in a Monsanto Processability Tester using a Garvey Die at 93° C. and 132° C. and piston speeds of 0.254 cm/min and 2.29 cm/min. Relative die swell was determined as described in Example 14. Data obtained is summarized in Tables XX and XXI and in FIGS. 2 and 4. Some of the die swell data presented is the average of two replications.

TABLE XX

| Blend | Wt % HFTAIC in Gel | Amount of Gel Component in Blend | Piston Speed (cm/min) | Extrusion Temp = 93° C.* Relative Die Swell (g) |
|---|---|---|---|---|
| A | 0.45 | 0 | 0.254 | 2.50 |
| B | 0.45 | 25 | 0.254 | 2.11 |
| C | 0.45 | 37.5 | 0.254 | 1.88 |
| D | 0.45 | 50 | 0.254 | 1.80 |
| A | 0.45 | 0 | 2.29 | 2.54 |
| B | 0.45 | 25 | 2.29 | 2.20 |
| C | 0.45 | 37.5 | 2.29 | 1.99 |
| D | 0.45 | 50 | 2.29 | 1.91 |

*At this low extrusion temperature all samples showed some tearing at the edges, making the errors in measuring relative die swell somewaht greated than at higher temperatures where extrudates were smoother.

TABLE XXI

| Blend | Wt % HFTAIC in Gel | Amount of Gel Component in Blend | Piston Speed (cm/min) | Extrusion Temp = 132° C.* Relative Die Swell (g) |
|---|---|---|---|---|
| A | 0.45 | 0 | 0.254 | 2.02 |
| B | 0.45 | 25 | 0.254 | 1.88 |
| C | 0.45 | 37.5 | 0.254 | 1.79 |
| D | 0.45 | 50 | 0.254 | 1.73 |
| A | 0.45 | 0 | 2.29 | 2.41 |
| B | 0.45 | 25 | 2.29 | 1.98 |
| C | 0.45 | 37.5 | 2.29 | 1.85 |
| D | 0.45 | 50 | 2.29 | 1.76 |

The data summarized above demonstrates the blend gives a product which exhibits less die swell than the sol polymer.

BRIEF DESCRIPTION OF THE DRAWINGS

FIG. 1 represents data derived from experiments where the extrusion temperature was 93° C. and the piston rate was 0.254 cm./min.

FIG. 2 represents data derived from experiments where the extrusion temperature was 93° C. and the piston rate was 2.29 cm./min.

FIG. 3 represents data derived from experiments where the extrusion temperature was 132° C. and the piston rate was 0.254 cm./min.

FIG. 4 represents data derived from experiments where the extrusion temperature was 132° C. and the piston rate was 2.29 cm./min.

INDUSTRIAL APPLICABILITY

Figure 1:
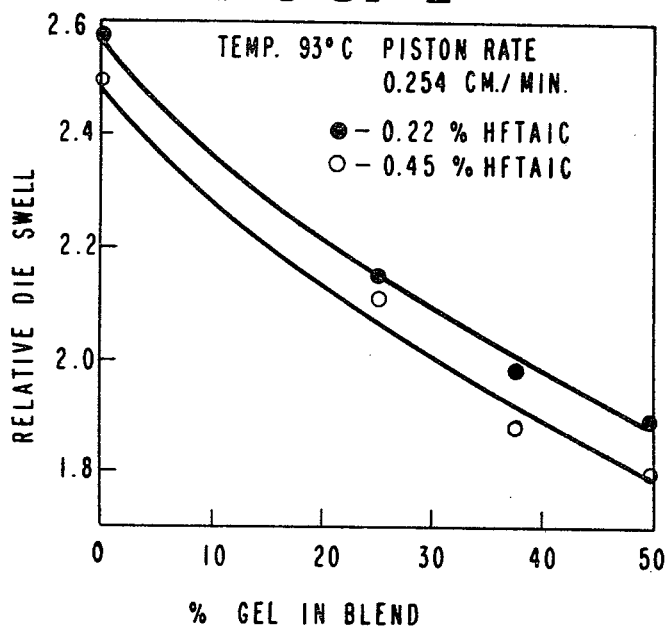
FIGS. 1–4 are graphs showing data derived from the experiments described in detail in Examples 14 and 15, which data is summarized in Tables XVII, XVIII, XX and XXI.
Figure 2:
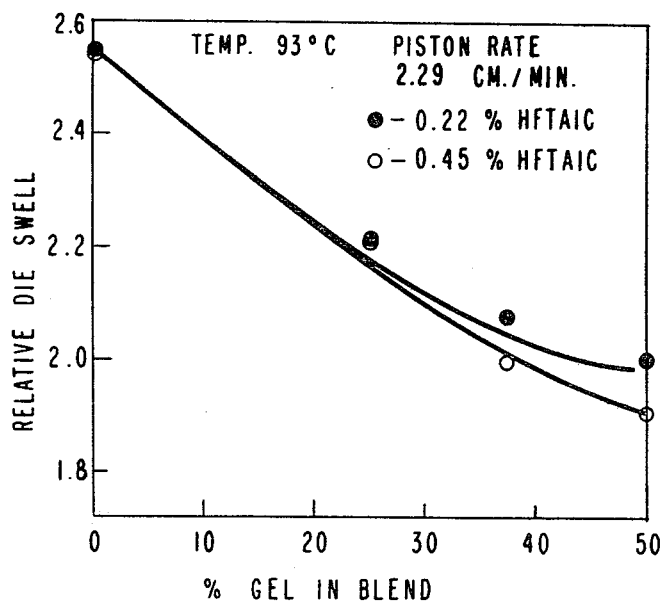
Figure 3:
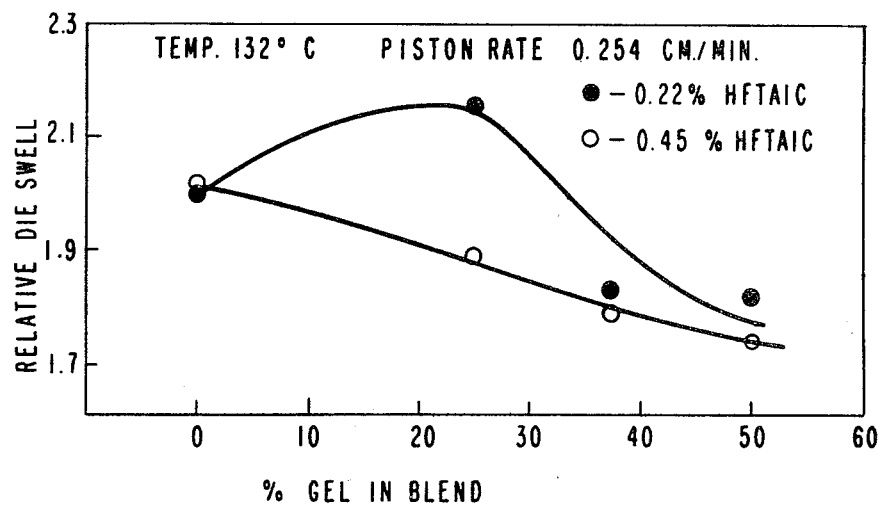
Figure 4:
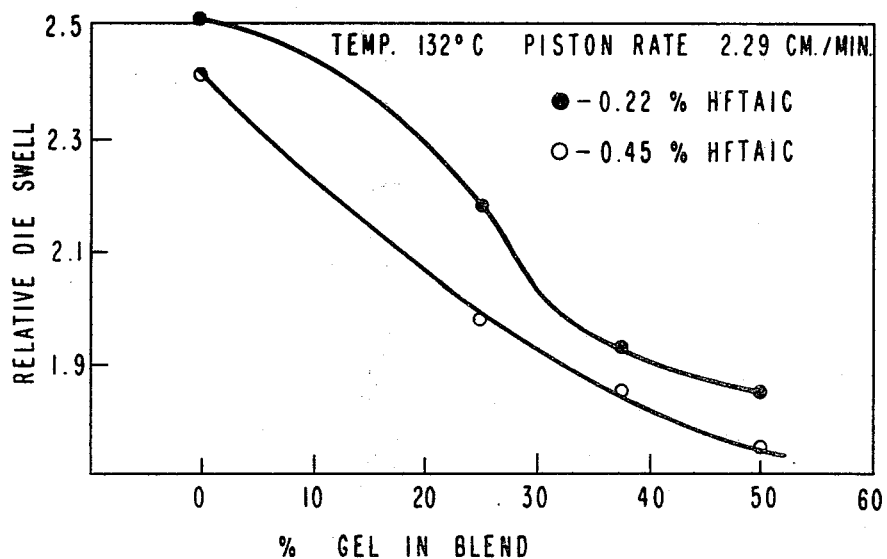

The fluoroelastomer blends of the present invention will be useful wherever prior fluoroelastomers have found utility, but these blends will be particularly useful and advantageous in situations requiring extrusion or milling of the fluoroelastomers, for example in manufacture of tubing, hose, sheet goods, and molding preforms.

BEST MODE

Insofar as the present invention comprises not only the preferred novel gelling agent, HFTAIC, but also the processes for making HFTAIC, HFTAIC gelled fluoroelastomer, and blends containing HFTAIC gelled fluoroelastomer, the best mode of practicing the present invention must relate to each of these aspects of the present invention. Beyond that, the best mode may vary depending on the particular desired end use and the specific requisite combination of properties for that use, especially as the designation of best mode relates to HFTAIC gelled fluoroelastomer and blends containing HFTAIC gelled fluoroelastomer. Within such constraints, the most preferred process for making HFTAIC is as described in Example 2; the most preferred HFTAIC gelled fluoroelastomer for the widest variety or most common end uses is as described in Example 7; and the most preferred blend containing HFTAIC gelled fluoroelastomer for the widest variety or most common end uses is as described in Example 15.

I claim:

1. A fluoroelastomer composition which comprises a blend of a gelled fluoroelastomer and a non-gelled fluoroelastomer, said gelled fluoroelastomer being a copolymer with interpolymerized units consisting essentially of vinylidene fluoride units, fluorine containing olefin units other than vinylidene fluoride units, optionally, at least one of perfluoroalkyl perfluorovinyl ether units, bromotrifluoroethylene units, bromotetrafluorobutene units or perfluorodivinyl ether units, and 0.05-3.0 weight percent of said gelled fluoroelastomer of 1,3,5-tris-(3,3-difluoro-2-propenyl)-s-triazine-2,4,6-(1H,3H,5H)-trione units, and said non-gelled fluoroelastomer being a copolymer with interpolymerized units consisting essentially of vinylidene fluoride units, fluorine containing olefin units other than vinylidene fluoride units, and, optionally, at least one of perfluoroalkyl perfluorovinyl ether units, bromotrifluoroethylene units, bromotetrafluorobutene units, or perfluorodivinyl ether units.

2. A fluoroelastomer composition of claim 1 wherein the gel content of the fluoroelastomer blend is 10-90 percent.

3. A fluoroelastomer composition of claim 1 wherein the gel content of the fluoroelastomer blend is 10-75 percent.

4. A fluoroelastomer composition of claim 1 wherein the gel content of the fluoroelastomer blend is 25-75 percent.

5. A fluoroelastomer composition of claim 1 wherein the gel content of the fluoroelastomer blend is 30-55 percent.

6. Vulcanized articles made from the composition of claim 1.

* * * * *